(12) United States Patent
Khillan

(10) Patent No.: US 6,448,470 B1
(45) Date of Patent: *Sep. 10, 2002

(54) TRANSGENIC COL2A1-NULL MICE EXPRESSING HUMAN COL2A1

(75) Inventor: Jaspal S. Khillan, Cherry Hill, NJ (US)

(73) Assignee: Thomas Jefferson University, Philadelphia, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/027,444

(22) Filed: Feb. 20, 1998

Related U.S. Application Data
(60) Provisional application No. 60/038,071, filed on Feb. 25, 1997.

(51) Int. Cl.$^7$ .................. A01K 67/00; C12N 15/85
(52) U.S. Cl. .................. 800/18; 800/9; 800/14; 435/325
(58) Field of Search .................. 800/2, 3, 8, 9, 800/13, 18, 14; 435/325

(56) References Cited

U.S. PATENT DOCUMENTS
5,545,808 A * 8/1996 Hew et al. .................. 800/2

OTHER PUBLICATIONS
Cheah et al. Matrix Biology, vol. 14, p. 409, 1994.*
Mullins et al. J. Clin. Invest., vol. 98, pp. S37–40, 1996.*
Moreadith et al. J. Mol. Med., vol. 75, pp. 208–216, 1997.*
Garofalo et al. PNAS, vol. 88, pp. 9648–9652, 1991.*
Wall Theriogenology, vol. 45, pp. 57–68, 1996.*
deCrombrugghe et al. J. Rheumatology, vol. 22, pp. 140–142, 1995.*
Li et al. Genes and Devel., vol. 9, pp. 2821–2830, 1995.*
Augee, 1992.*
Li et al. (Genes & Devel. (Nov. 15, 1995) 9 (22) 2821–30).*
Cheah et al. (Matrix Biology 14 (5). 1994. 409).*
Whittington et al. (Nature Genetics, (Feb. 1995) 9 (2) 197–201).*
Vandenberg et al. (Proc. Natl. Acad. Sci. USA (1991) Sep. 1 88 (17) 7640–4).*
Dombrowicz et al. (J. Immunol. (Aug. 15, 1996) 157 (4) 1645–51).*
Lefebvre et al. ( Matrix Biol. (Aug. 1994) 14 (4) 329–35).*
Rosati et al. (Nature Genetics, Oct. 8, 1994 (2) 129–35).*
Charreau et al. (Transgenic research, (Jul. 1996) 5 (4) 223–34) (Abstract).*
NIH Reports, Dec. 1995.*
Wall R. J. Theriogenology, 45, 57–68, 1996.*
Houdebine L.–M. J. Biotechnol. 34, 1994, 269–287.*
Wagner et al. Genetic Engineering: Principles and Methods. 1988, vol. 10, p221–246, (p. 221 and p. 238 Only).*

Ala–Kokko et al., Single base mutation in the type II procollagen gene (COL2A1) as a cause of primary osteoarthritis associated with a mild chondrodysplasia, (1990) Proc. Natl. Acad. Sci. USA, 87:6565–68.

Bonadio et al., "Transgenic mouse model of the mild dominant form of osteogenesis imperfecta", (1990) Proc. Natl. Acad. Sci. USA, 87:7145–49.

Bradley et al., "Formation of germ–line chimaeras from embryo=derived teratocarcinoma cell lines", (1984) Nature 309:255–256.

de Crombrugghe et al., "Transgenic Mice with Deficiencies in Cartilage Collagens: Possible Models for Gene Therapy", (1995) J. Rheumatol., 22:1 Supp. 43:140–142.

Drabek et al., Correction of the X–linked immunodeficiency phenotype by transgenic expression of human Bruton tyrosine kinase under the control of the class II major histocompatibility complex Ea locus control region, (1997) Proc. Natl Acad. Sci. USA 94:610.

Engel and Prockop, "The Zipper–like folding of collagen triple helices and the effects of mutations that disrupt the zipper", (1991) Annu. Rev. Biophys. Biophys. Chem. 20:137–52.

Fleischmaier et al., "Structure, Molecular Biology, and Pathology of Collagen", (1990) Ann. NY Acad. Sci. 580:161–175.

Garofalo et al., "Assembly of cartilage collagen fibrils is disrupted by overexpression of normal type II collagen in transgenic mice", (1993) Proc. Natl. Acad. Sci. USA, 90:3825–29.

Nakata, et al., "Osteoarthritis associated with mild chondrodysplasia in transgenic mice expression α1 (IX) collagen chains with a central deletion", (1993) Proc. Natl. Acad. Sci. USA 90:2870.

Garofalo et al., "Reduced amounts of cartilage collagen fibrils and growth plate anomalies in transgenic mice harboring a glycine–to–cysteine mutation in the mouse type II procollagen $α^1$–chain gene", (1991) Proc. Natl. Acad. Sci. USA, 88:9648–52.

Helminen et al., "An Inbred Line of Transgenic Mice Expression an Internally Deleted Gene for Type II Procollagen (COL2A1)", (1993) J. Clin. Invest., 92:582–95.

Hulmes, "The collagen superfamily—diverse structures and assemblies", (1992) Essays Biochem., 27:49–67.

Kivirikko, "Collagens and their Abnormalities in a Wide Spectrum of Diseases", (1993) Ann. Med., 25:113–26.

(List continued on next page.)

Primary Examiner—Michael C. Wilson
(74) Attorney, Agent, or Firm—ReedSmith LLP; William J. McNichol, Jr.; Nanda P. B. A. Kumar

(57) ABSTRACT

Transgenic animals which express human collagen gene and have an inactivated endogenous collagen gene are provided. Compositions comprising humanized chondrocytes isolated from these transgenic animals are also provided. In addition, methods of screening potential therapeutics for cartilage related disorders in these animals are provided.

3 Claims, 3 Drawing Sheets

OTHER PUBLICATIONS

Kuivaniemi et al., "Mutations in collagen genes: causes of rare and some common diseases in humans", (1991) *FASEB J.*, 5:2052–60.

Li et al., "Transgenic mice with targeted inactivation of the Col2a1 gene for collagen II develop a skeleton with membranous and periosteal bone but no endochondral bone", (1995) *Genes & Development* 9:2821–2830.

Lanza et al., "Encapsulated cell technology", (1996) *Nature Biotechnology* 14:1107–1111.

Maga, E.A. and J.D. Murray, "Mammary Gland Expression of Transgenes and the Potential for Altering the Properties of Milk", (1995) *Biotechnology* 13:1452–1456.

Metsaranta et al., "Chondrodysplasia in Transgenic Mice Harboring a 15–Amino Acid Deletion in the Triple Helical Domain of Proα (II) Collagen Chain", (1992) *J. Cell Biol.*, 118:203–12.

Prockop and Kivirikko, "Collagens: Molecular Biology, Diseases, and Potentials for Therapy", (1995) *Annu. Rev. Biochem.* 64:403–34.

Ritvaniemi et al., "Identification of Col2A1 Gene Mutations in Patients with Chondrodysplasias and Familial Osteoarthritis", (1995) *Arthritis Rheum.*, 38:999–1004.

Schenkel et al., "Functional rescue of the glomerulosclerosis phenotype in Mpv17 mice by transgenesis with the human Mpv17 homologue", (1995) *Kid. Inter.* 48:80.

Schoonjans et al., "Pluripotential Rabbit Embryonic Stem (ES) Cells Are Capable of Forming Overt Coat Color Chimeras Following Injection Into Blastocysts", (1996) *Molecular Reproduction and Development* 45:439–443.

Spranger et al., "The type II collagenopathies: a spectrum of chondrodysplasias", (1994) *Eur. J. Pediatr.*, 153:56–65.

Vandenberg et al., "Expression of a partially deleted gene of human type II procollagen (COL2A1) in transgenic mice produces a chondrodysplasia", (1991) *Proc. Natl. Acad. Sci. USA*, 88:7640–44.

Vikkula et al., "Type II Collagen Mutations in Rare and Common Cartilage Diseases", (1994) *Ann. Med.*, 26:107–14.

Vuorio, E., and de Crombrugghe, B., "The Family of Collagen Genes", (1990) *Ann. Rev. Biochem.* 59:837–872.

Williams et al., "Rapid Detection of Mutations by Conformation–Sensitive Gel Electrophoresis. Application to the Indentification of a Fourth Family with the $Arg^{519}$–Cys Substitution and Three New Mutations in the Type II Procollagen Gene", (1994) *Matrix Biol.*, 14:391.

Wu et al., "Human–Mouse Interspecies Collagen I Heterotrimer Is Functional during Embryonic Development of Mov13 Mutant Mouse Embryos", (1990) *Mol. and Cell Biol.*, 10:1452–60.

* cited by examiner

TRANSGENIC COL2A1-NULL MICE EXPRESSING HUMAN COL2A1

This application claims the benefit of U.S. Provisional Application No. 60/038,071, filed Feb. 25, 1997.

BACKGROUND OF THE INVENTION

Collagens belong to an ever-expanding family of proteins that have the capacity to form extracellular fibrils or network-like structures and fulfill a variety of essential biological functions in vertebrates (Fleischmaier et al. (1990) Ann. N.Y. Acad. Sci. 580:161–175; Engel and Prockop (1991) Annu. Rev. Biophys. Biophys. Chem. 20:137–52; Prockop and Kivirikko (1995) Annu. Rev. Biochem. 64:403–34). Structurally, they are characterized by the presence of several repeats of the amino acid sequence -Gly-X-Y-(where X=proline and Y=4-hydroxyproline). Additionally, they have the potential for the generation of three chains with such repeated sequences that fold into a characteristic triple helix. This assembly and characteristic folding conformation influences the ability of the collagens to polymerize. A correctly assembled triple helix is relatively rigid which is important for the biological function of the protein.

The most abundant types of collagen in the body are those that form fibrils (types I, II, III, V, and XI) (Hulmes (1992) Essays Biochem., 27:49–67). Type I collagen has the most extensive distribution and is consequently the most abundant of the fibril-forming collagens. It is present in most connective tissues. Type II collagen is the second most abundant collagen but has a somewhat more selective tissue distribution, being found in both the cartilage and vitreous humor of the eye. Due to the widespread distribution and essential function of these collagens, over 300 different mutations in fibril collagen genes have been identified thus far in patients afflicted with a variety of diseases.

The elucidation of mutations in human patients through familial genetic analysis has identified over 50 alterations alone in the gene for collagen type II (COL2A1), the most abundant protein in cartilage (Kuivaniemi et al. (1991) FASEB J., 5:2052–60; Kivirikko (1993) Ann. Med., 25:113–26). These mutations in the COL2A1 gene cause a spectrum of cartilage defects ranging from moderate phenotypes to lethal forms of chondrodysplasia and skeletal deformities (Vikkula et al. (1994) Ann. Med., 26:107–14). Mutations in COL2A1 are also found in approximately 2% of patients with early onset familial osteoarthritis (OA) (Ritvaniemi et al. (1995) Arthritis Rheum., 38:999–1004). Specific mutations found in patients with OA include a substitution of cysteine for arginine at amino acid 519 of the alpha1 (II) chain, and serine for glycine mutations at positions alpha1-274 and alpha1-976 (Williams et al. (1994) Matrix Biol., 14:391; Ala-Kokko et al. (1990) Proc. Natl. Acad. Sci. USA, 87:6565–68; Spranger et al. (1994) Eur. J. Pediatr., 153:56–65).

Several studies have been performed using transgenic mice in which mutated collagen genes were randomly inserted to produce dominant negative effects. Additionally, studies have been carried out involving the inactivation of collagen genes either by viral insertion (Bonadio et al. (1990) Proc. Natl. Acad. Sci. USA, 87:7145–49) or by knock-out of collagen genes or portions of collagen genes (Li et al. (1995) Genes and Dev., 9:2821–30). Studies with transgenic animal models have shown that mutated human COL2A1 gene constructs can cause phenotypes similar to chondrodysplasia seen in human patients with dwarfism, a short snout, a cranial bulge, cleft palate, and delayed mineralization of the bone (Vandenberg et al. (1991) Proc. Natl. Acad. Sci. USA, 88:7640–44). Expression of specifically mutated mouse COL2A1 genes resulted in similar phenotypes of severe chondrodysplasia (Nakata et al. (1991) Proc. Natl. Acad. Sci. USA, 88:9648–52; Metsaranta et al. (1992) J. Cell Biol., 118:203–12). In older mice from the same lines, the evidence of chondrodysplasia was less marked, and the most striking features were degenerative changes of articular cartilage similar to osteoarthritis (Helminen et al. (1993) J. Clin. Invest., 92:582–95). Overexpression of a normal mouse COL2A1 gene in transgenic mice produced abnormally thick collagen fibrils in cartilage, apparently because of an imbalance in the amounts of collagen being synthesized in the tissues (Garofalo et al. (1993) Proc. Natl. Acad. Sci. USA, 90:3825–29).

An experimental approach for studying the physiological effects of mutations on collagen function that has met with some success is introduction of a gene that encodes one polypeptide component of collagen into animals that express the other component. The transferred gene may also be engineered to carry defined mutations. The endogenous gene corresponding to the transferred gene is necessarily functionally deleted with no effect on the other subunit component.

Wu et al. (1990) Mol. and Cell Biol., 10:1452–60, used this approach to show that a human-mouse interspecies collagen I heterotrimer does form and is functional in embryonic development of transgenic mouse embryos. However, rescue of the phenotype is only partial, since embryos die soon after birth. Similarly, Vandenberg et al. (1991) Proc Natl. Acad. Sci. USA, 88:7640–44 prepared transgenic mice expressing a minigene version of the human COL2A1 gene along with the mouse gene. In cultured chondrocytes prepared from the transgenic mice, the minigene was expressed as shortened pro-alpha1 (II) chains that were disulfide-linked to normal mouse pro-alpha1 (II) chains. It was suggested that the presence of the shortened pro-alpha chain in a procollagen molecule can prevent folding into a stable triple helix that results in degradation of normal genes in a phenomenon known as procollagen suicide.

de Crombrugghe et al. (1995) J. Rheumatol., 22:1 Supp. 43:140–142 generated transgenic mice by introducing dominant negative mutations in the mouse COL2A1 gene. Mice homozygous for the mutant transgene died at birth but showed a phenotype of severe chondrodysplasia with skeletal anomalies. Electron microscopic analysis revealed an absence of normal collagen fibrils in cartilage. Mice heterozygous for the transgene, however, showed no significant abnormalities at birth but developed clear signs of osteoarthritis with erosion of cartilage structure in joints by six to nine months of age. Severity of the phenotype was linked to expression of the mutant gene. Thus, transgenic animals, if engineered with specific mutations, provide a useful system to understand the pathoetiology of type II collagen diseases, particularly, OA and to evaluate therapeutic drugs for blocking degenerative changes in cartilage.

Transgenic mice capable of expressing the human collagen gene and not the mouse collagen gene have now been developed. These mice are especially useful in the development of compositions and methods of treating human type II collagen related diseases. Furthermore, the chondrocytes, the cells that synthesize procollagen type II from the transgenic animals that express the normal human COL2A1 gene, provide a source of biomaterial to treat cartilage related diseases.

OBJECTS OF THE INVENTION

An object of the present invention is to produce a transgenic mouse model system capable of expressing the human collagen gene wherein the endogenous mouse collagen gene is inactivated.

Another object of the present invention is the utilization of the transgenic mouse model system to develop compositions and methods for the treatment of cartilage related disorders.

Yet another object of the present invention is the production of quantities of biomaterials for the treatment of cartilage related disorders.

DETAILED DESCRIPTION OF THE INVENTION

Figure 1:
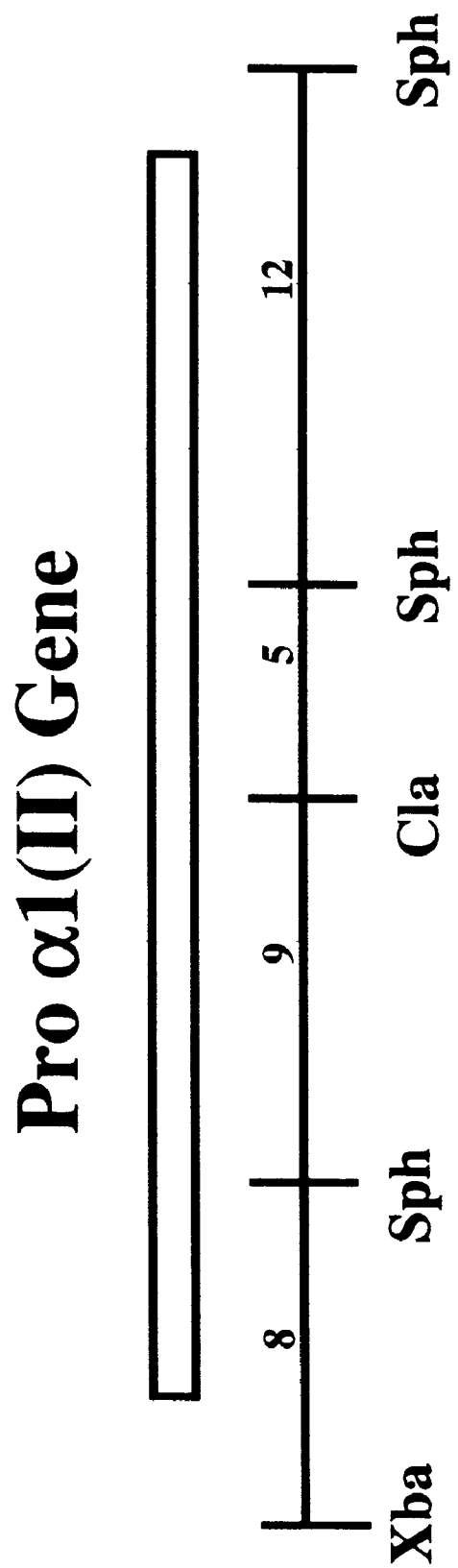
FIG. 1 shows a schematic of a construct of the normal human COL2A1 gene.

The treatment of various human diseases has always been limited by the availability of specific cell types representing affected tissues. Thus, a major focus of biotechnology during the past decade has been to develop genetically engineered cells that express specific bioactive substances. The application of bioengineered or primary cells that produce a desired product offers an enormous potential to treat human diseases. A large population in the United States and other parts of the world is suffering from the debilitating and degenerative defects of the cartilage. Despite several decades of research, the need still remains for a system to study the progressive degeneration of the cartilage. Further, the availability of adult human cartilage for various types of experimentation is extremely limited. Since it is impossible to perform these kinds of studies directly on patients, an animal model with humanized cartilage would be a highly valuable system. Since the mouse collagen protein can associate with human collagen chains, it is important that the endogenous mouse gene be inactivated.

A unique approach has now been developed which combines gene knockout and gene transfer technology in the early embryo, to generate such an animal model. These animals are useful in the study of the progression of cartilage diseases and the development of strategies to cure cartilage related diseases by therapeutic drugs or by somatic cell therapy. Further, these animals serve as a source of biomaterial for the treatment of cartilage related diseases in patients.

Transgenic lines of mice have now been created in which the endogenous type II collagen gene is inactivated by insertional mutagenesis. These mutant mice do not produce normal cartilage or long bones. Transgenic lines of mice have also been created that express the normal human COL2A1 gene. The breeding of these two types of animals results in a progeny with the human collagen gene being expressed on the inactivated background of the endogenous COL2A1 gene. It is believed that the cartilage of these animals contains only human collagen type II, referred to herein as "humanized cartilage".

Isolated chondrocytes from these transgenic mice serve as a source of biomaterial for somatic cell therapies in humans either directly or using technologies such as encapsulated cell technology. As discussed by Lanza et al. in *Nature Biotechnology* (1996) 14:1107–1111, the potential therapeutic applications of encapsulated cells are enormous. A number of encapsulation systems have now been developed wherein living cells are separated from the immune system of the body by a synthetic, semipermeable membrane which allows for the free exchange of nutrients, oxygen and biotherapeutic substances between the blood and the encapsulated cells but prevents high molecular weight substances such as immunocytes, antibodies and other transplant rejection effector mechanisms from contacting the cells. A number of cartilage related disorders in humans result from insufficient amounts of normal type II collagen or the presence of defective type II collagen. Thus, it is believed that compositions of the present invention, comprising chondrocytes isolated from the transgenic animals of the present invention which express human type II collagen, referred to herein as "humanized chondrocytes", injected directly along with immunosuppressor drugs or encapsulated into a synthetic semipermeable membrane and then injected into the joints of an individual suffering from a cartilage related disorder, will be useful in treating these disorders.

Collagen genes have been found to be highly homologous between species (Vuorio, E., and de Crombrugghe, B. (1990) *Ann. Rev. Biochem.* 59:837–872). Accordingly, in similar fashion to the transgenic mice, larger mammalian non-human transgenic animals can be produced and the chondrocytes, with human type II collagen, can be isolated in larger quantities for xeno-transplantation. The chondrocytes of these larger transgenic animals may be a source for the large scale production of processed and natural collagen II for the oral treatment of rheumatoid arthritis. By "larger animals" it is meant to include, but is not limited to, pigs, cows, rabbits, goats and monkeys. Methods of developing transgenic animals of these larger species are currently under development by those skilled in the art. A review of such methods is provided in Maga, E. A. and J. D. Murray (1995) *Biotechnology* 13:1452–1456. For example, Schoonjans et al. (1996) *Molecular Reproduction and Development* 45:439–443 disclose a method of producing chimeric rabbits.

The isolated, cultured chondrocytes of these animals are a source of human collagen type II since there is no interference from the endogenous protein. The progress of cell therapy has been limited due to the non-availability of specific cell types to express proteins. In one embodiment, the cells produced in the animals especially in large species can be directly injected into the joints of the patients to cure the cartilage defects related to type II collagen along with an immunosuppressor drug. In another embodiment, the cells can be encapsulated in a synthetic, selectively permeable membrane to prevent the rejection of cells and transferred to the joints of the patients. Some cell types have been shown to be active for several months in animals following encapsulation. Lanza et al. (1996) *Nature Biotechnology* 14:1107–1111.

In addition, the transgenic animals of the present invention provide a powerful system for basic studies such as fibril formation which is otherwise difficult to conduct due to the limited availability of cartilage from patients.

Previously, such studies could only be carried out in vitro by DNA transfection assays in cultured chondrocytes. However, in the present invention, transgenic animals can be generated which contain specific mutations in the collagen gene similar to that observed in certain patient groups. Breeding of these animals with the animals that express normal human gene simulates exactly the defects of the cartilage of patients with that particular mutation. Alternatively, the mutations can be introduced directly into these mice via homologous recombination in embryonic stem cells. Since mutated human protein chains will compete with the normal human chains only, it is believed that the degenerative changes observed in the animals will mimic the same cartilage defects observed in those patients. Once such type of progeny is obtained, it becomes possible to understand the mechanisms of disease progression and to predict the osteoarthritic changes expected in those patients thereby facilitating the development of modalities to intervene and to evaluate somatic cell therapy either in utero or during later stages in life.

In these studies, animals expressing human collagen type II are crossed with transgenic animals with a specific selected mutation to obtain mice with only normal and/or mutated human genes on the endogenous null background. Over 50 alterations alone in the gene for collagen type II (COL2A1) have been defined and are well known to those skilled in the art. Thus, only a few are described in detail herein.

For example, several lines of transgenic animals having the COL2A1 minigene have been produced. Mice expressing the minigene display a phenotype of chondrodysplasia. Vandenberg et al. (1991) *Proc Natl. Acad. Sci. USA*, 88:7640–44. The mice from this line can be crossed with the COL2A1$^{+/-}$ mice. Alternatively, the arginine at position 75 of the COL2A1 gene is mutated to a cysteine. This mutation has been identified in two apparently unrelated families with spondyloepiphyseal dysplasia tarda associated with severed articular and extra articular calcification. In another embodiment, 3 bp located 46 bp 5' to exon 40 of the COL2A1 gene are deleted. This mutation, referred to as the "stump mutation" has been observed in two patients with heritable osteochondrodysplasia and precocious osteoarthritis. The products of this mutated gene are not spliced correctly. Similar observations have been made when the DNA from this region is transfected into Hela cells. The deletion in the region is believed to be responsible for the binding of transcription factors. Such animals will be representative of the exact human situation for the particular mutation.

Transgenic mice with specific mutations in the human COL2A1 transgene provide an excellent test model to predict onset and progression of the degenerative changes and to design and test drug formulations for treatment of cartilage related disorders resulting from a specific mutation in humans. Different mutations in the COL2A1 gene have been identified in different families with overlapping cartilage defects. Therefore, it is likely that therapy applicable to patients with one mutation may not be effective for patients with other mutations. Accordingly, transgenic animals with exact mutations would be a useful system on which to test and design therapeutic drugs for the specific mutation unique to those families, without side effects. Potential therapeutic drugs are administered to the animals having a specific mutation in the human COL2A1 gene. The animal is then monitored for changes in symptoms resulting from the cartilage related disorder.

For example, it has been hypothesized that the Arg75-Cys mutation results in inter-chain disulfide bonding which leads to calcium pyrophosphate dihydrate depositions. Transgenic animals having this mutation provide an excellent modeling for confirming this hypothesis as well as to test drug therapies based on the reducing agents.

Alternatively, transgenic mice having the stump mutation will provide a useful system to study COL2A1 gene regulation since this mutation prevents the proper splicing of RNA. These animals will also be useful in studying the mechanisms of alternate splicing of pre mRNA in collagen genes.

Animals expressing the COL2A1 minigene are useful in determining whether the shortened procollagen chains are capable of forming functional collagen molecules and whether the complete region of the triple helix is essential for the formation of functional collagen molecule. Data derived from such studies in these animals will have important implications for the basic studies of fibril formation and the role of different D periods of collagens in an in vivo situation.

In a further embodiment, these animals would be useful for developing strategies for the treatment of cartilage diseases caused by mutations in other cartilage specific genes.

Transgenic lines of mice may be prepared by methods known to those of skill in the art. In a preferred embodiment, a normal DNA clone of the human COL2A1 gene is microinjected into mouse embryos. Transgenic lines are then established from the founder mice.

Transgenic lines of mice were prepared by microinjecting an approximately 38 kb genomic clone of normal human COL2A1 gene by methods well known to those of skill in the art. Transgenic mice were phenotypically normal and were able to breed normally. Heterozygous animals (COL2A1h$^{+/-}$) from one of the lines were crossed with hemizygous COL2A1 mutant (COL2A1m$^{+/-}$) mice and the progeny were analyzed by polymerase chain reaction (PCR) analysis using primers specific for the human transgene and the COL2A1 mutation. Two of the eight pups born showed the amplification of expected fragments of 330 bp and 547 bp specific for the COL2A1 mutation and human gene, respectively, indicating that these animals are double hemizygous (COL2A1 m$^{+/-}$, COL2A1 h$^{+/-}$) for the mutant allele and human transgene. Hemizygous pups for COL2A1 mutation are usually about 30% smaller at birth than the normal littermates (Li et al. (1995) Gene Devel. 9:2821). However, the double hemizygous animals were almost normal, suggesting that human protein may have compensated for the loss of the mutated allele.

Expression of human collagen in the transgenic mice was confirmed by Western blot analysis using antibodies specific for human collagen type II of chondrocytes isolated from the xiphoid cartilage of 3 to 4 week old normal and double hemizygous (COL2A1 m$^{-/-}$, COL2A1 h$^{+/-}$) mice. The chondrocytes from transgenic mice expressed high levels of human type II collagen. Only a non-specific band of weak intensity was observed in the chondrocytes from normal animals, Furthermore, the analysis of supernatant from chondrocyte cultures showed that collagen type II is also secreted in the medium. Protein from a human COL2A1 minigene can associate with the mouse chains to form hybrid molecules. Accordingly, it is believed that in these mice the human collagen alpha chains associated with endogenous collagen chains. This rescue may be through the human collagen chains either alone or in association with mouse collagen alpha chains to form normal fibrils.

To investigate whether the human collagen II is able to rescue the phenotype in null (COL2A1 m$^{-/-}$) mice, double hemizygous animals from the previous experiments were mated with each other. Eight pups were born from this mating, none of whom displayed any obvious phenotype. PCR analysis revealed that DNA from two pups amplified only a single fragment of 357 bp specific for the targeted allele, and did not amplify the 859 bp fragment specific for the normal allele, thus indicating that these animals are homozygous for the COL2A1 mutation. In contrast, heterozygous pups amplified both the fragments. The DNA was further analyzed by human gene specific primers. The DNA from the same two animals amplified a 547 bp band confirming that the rescue of normal phenotype in these animals is due to human collagen type II. Since about 25% of the animals in the litter were homozygous, it confirmed the Mendelian transmission of the mutated allele. Both pups were phenotypically normal and did not show any size or weight difference at birth as compared to their normal littermates. Subsequent matings of other double hemizygotes reproducibly produced progeny that survived due to human COL2A1 gene (see Table 1).

TABLE 1

Breeding of Double Heterozygous Animals

| Litter Number | Number of Pups | Number of Homozygotes with Human Gene | Number of Survivors |
| --- | --- | --- | --- |
| 1 | 7 | 1 | 1 |
| 2 | 9 | 3* | 2 |
| 3 | 5 | 1 | 1 |
| 4 | 8 | 2 | 2 |
| 5 | 8 | 1 | 1 |
| Total | 37 | 8 | 7 |

*One pup was cannibalized by the mother.

To determine whether the animals had complete skeletons, newborn pups were stained with alizarin red S. Homozygous mutant (COL2A1 m$^{-/-}$) mice displayed severe abnormalities of the skeleton such as a small rib cage, abnormal vertebral column, and abnormal long bones with only periosteal bone present. No mineralization of the caudal vertebrae was observed. In contrast, the homozygotes with a human COL2A1 gene (COL2A1 m$^{-/-}$, COL2A1 h$^{+/-}$) displayed normal skeletal structures with normal size rib cage and well mineralized caudal vertebra similar to that seen in a normal littermate.

Figure 3:
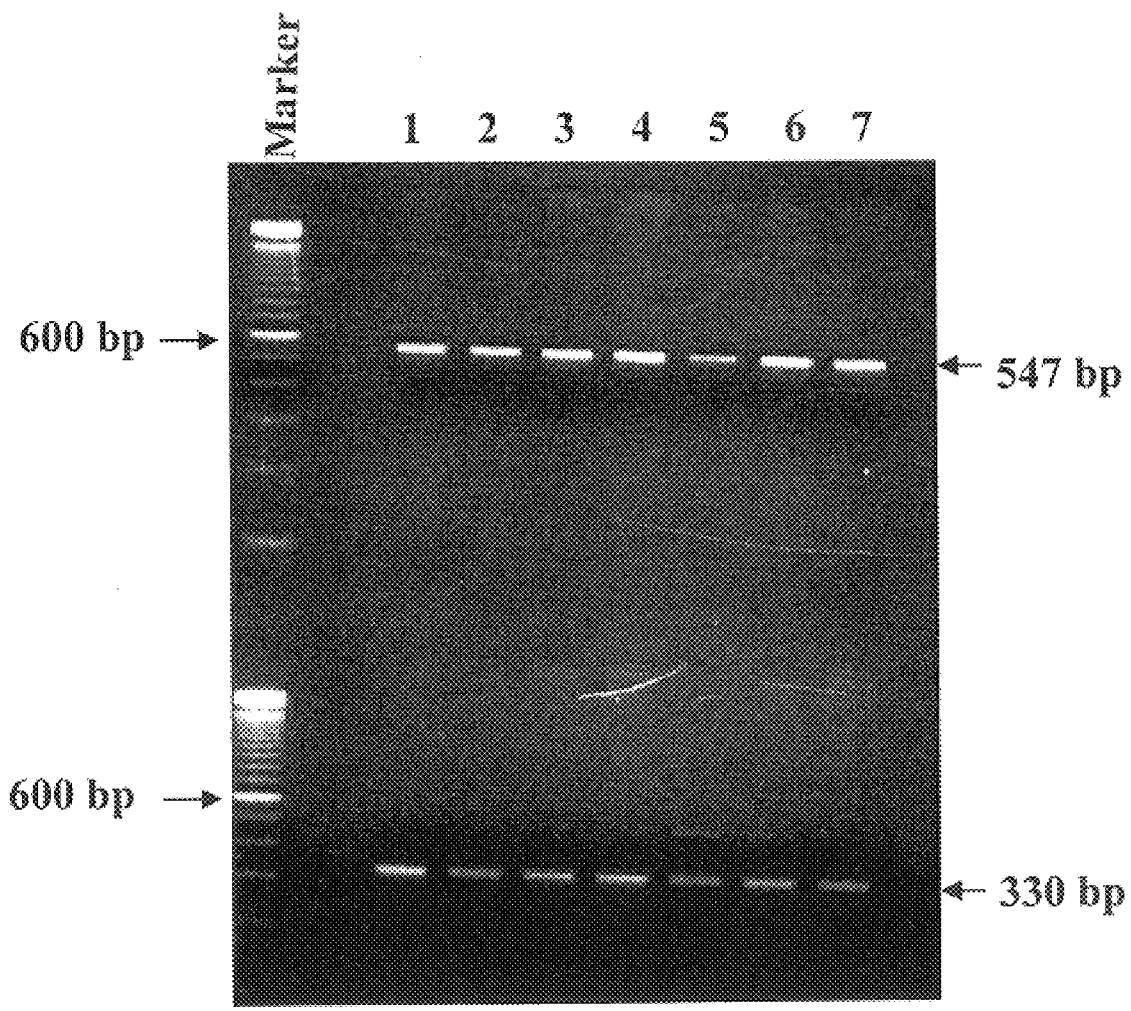
FIG. 3 shows the results from the PCR analysis of progeny of a cross between a double homozygous male and a wild type female. Seven pups born from this mating were tested for COL2A1 mutation (neomycin gene) and human COL2A1 gene. DNA from all the pups amplified both human specific (547 bp) and neo specific (330 bp) fragments.

Adult mice with the human transgene appeared healthy and normal and were fertile. An almost equal number of male and female animals were obtained suggesting that there was no gender bias for survival. No obvious differences in weight or growth rate between normal and transgenic mice were observed either at birth or at puberty. Breeding of a male with a wildtype female produced a litter of normal size in which all the progeny were positive for the COL2A1 mutation and human gene see FIG. 3) further confirming that the mouse is homozygous for the COL2A1 mutation as well as the human gene.

Skeletons of newborn pups from a cross between double heterozygous animals were fixed in paraformaldehyde, embedded, sectioned, and processed for further examination by histological analysis. Hemotoxylin eosin staining of sections from the metatarsal-tarsal region of the hind limbs of normal, null mutant, and a null mutant with the human gene showed a complete absence of endochondral bone in the null mouse. The chondrocytes showed a lack of columbar organization and were dispersed. A small population of large cells which resembled early stages of hypertrophic chondrocytes was seen at the peripheral region. In contrast, a comparable section from the null mutant with the human gene showed a well organized growth plate containing columns of chondrocytes and a normal zone of resting chondrocytes similar to that seen in the normal littermate. Alcian blue staining of the adjacent sections further confirmed these observations. The section from null mutant mouse also stained positive with alcian blue suggesting the presence of sulfated proteoglycans, typical of cartilage matrix, although no obvious cartilage phenotype was observed.

Staining of sections with alizarin red demonstrated normal endochondral and periosteal bone formation in rescued mouse as seen in a normal littermate, whereas COL2A1 null mouse showed staining of only the periosteal bone confirming the observations on the complete skeleton.

Functional equivalence of human proteins such as Bruton tyrosine kinase (Drabek et al. (1997) *Proc. Natl. Acad. Sci. USA* 94:610) and Mpv17 (Schenkel et al. (1995) *Kid. Inter.* 48:80) in heterologous mouse systems has been documented before. However, the functional conservation of structural proteins that undergo complex interactions with other components of the cell or tissue has not been demonstrated. The data described above provide the first evidence for the conservation of function of type II collagen between mouse and human. The human collagen type II rescued a severe developmental phenotype of endochondral bone in COL2A1-null mice. Further, the animals displayed complete absence of any phenotype which contrasts the earlier reports that even expression of normal murine COL2A1 transgene can have serious consequences in mice (Garofalo et al. (1993) *Proc. Natl. Acad. Sci. USA* 90:2870). Therefore, the sequences present in the human transgene are sufficient for the correct temporal and spatial expression. These data demonstrate that mice with the human COL2A1 gene provide a model to study the effects of specific human mutations in pathogenesis as well as a prognostic system to test for disease-cause relationships at the genetic level. Further, since type II collagen comprises a major component of cartilage, the cartilage of these mice is essentially humanized and thus provides a source of bio-material for tissue research and in the repair cartilage defects.

The following examples are provided for illustrative purposes only and are not intended to limit the invention.

EXAMPLES

Example 1

Preparation of Transgenic Mice

Animals were prepared by injecting about 600–800 copies of a Sal1—Sal1 fragment of approximately 38 kb from human COL2A1 genomic clone into the male pronucleus of FVB/N embryos. The DNA contains about 4.5 kb of the 5'-upstream and about 3 kb of the 3'-sequences beyond the major polyadenylation signal. The mice were screened by PCR analysis using E1F (5'-TTGGGTGTGA-TCTGAAGCATC-3' (SEQ ID NO: 1)) and E1R (5'-AGCCAGCTAAGTCTGTCTGTA-3' (SEQ ID NO: 2)) primers that amplify a fragment of 547 bp specific for human gene. The conditions of PCR were 94° C. for 30 seconds, 56° C. for 30 seconds, and 72° C. for one minute for 30 cycles in PEC 9600 thermocycler. The animals for COL2A1 mutation were screened by neo-2 (5'-TCGCGATT-GAACAAGATGG-3' (SEQ ID NO: 3)) and neo-3 (5'-GAGCAAGGTGAGATGACAGG-3' (SEQ ID NO: 4)) primers specific for neomycin gene that amplify a band of 330 bp. Hemizygous or homozygous animals for COL2A1 mutation were analyzed with three oligonucleotide primers: neo-7 (5'-GCTATCAGGACATAGCGTTGG-3' (SEQ ID NO: 5)) which is specific for neomycin gene; E-36 (5'-GGAGTCAGAGCACTGGTCATG-3' (SEQ ID NO: 6)) which is specific for Exon 36; and I-34 (5'-CTGTTGCTTATAGGACTCAGG-3' (SEQ ID NO: 7)) which is specific for intron 34 of the mouse COL2A1. The primers amplify a band of 859 bp from the normal allele and a 357 bp from the targeted allele.

Example 2

Preparation of Gene Knockout Animals

The gene knockout (KO) is performed by electroporation of a selected targeting cassette into embryonic stem (ES) cells. In one embodiment, the targeting cassette contains selectable markers such as neomycin and herpes simplex virus thymidine kinase inserted into portions of the COL2A1 gene. Specific mutations in the target gene can be introduced by homologous recombination and the gene targeted cells selected for G418 resistance and gancyclovir sensitivity. The selected clones are microinjected into the cavity of a blastocyst in accordance with known procedures such as those described by Bradley et al. (1984) *Nature* 309:255–256. The embryos are transferred into pseudopregnant females, by methods known to those of skill in the art, to obtain chimeric animals. These chimeras are crossed with normal animals to obtain germline transmission of the mutated gene. Two heterozygous animals are crossed, in accordance with art-known methods, to obtain homozygous animals for the specific mutation in which no product of the gene will be synthesized. See, for example, Li et al. (1995) *Genes & Development* 9:2821–2830.

Example 3

Preparation of Hybrid Animals

Figure 2:
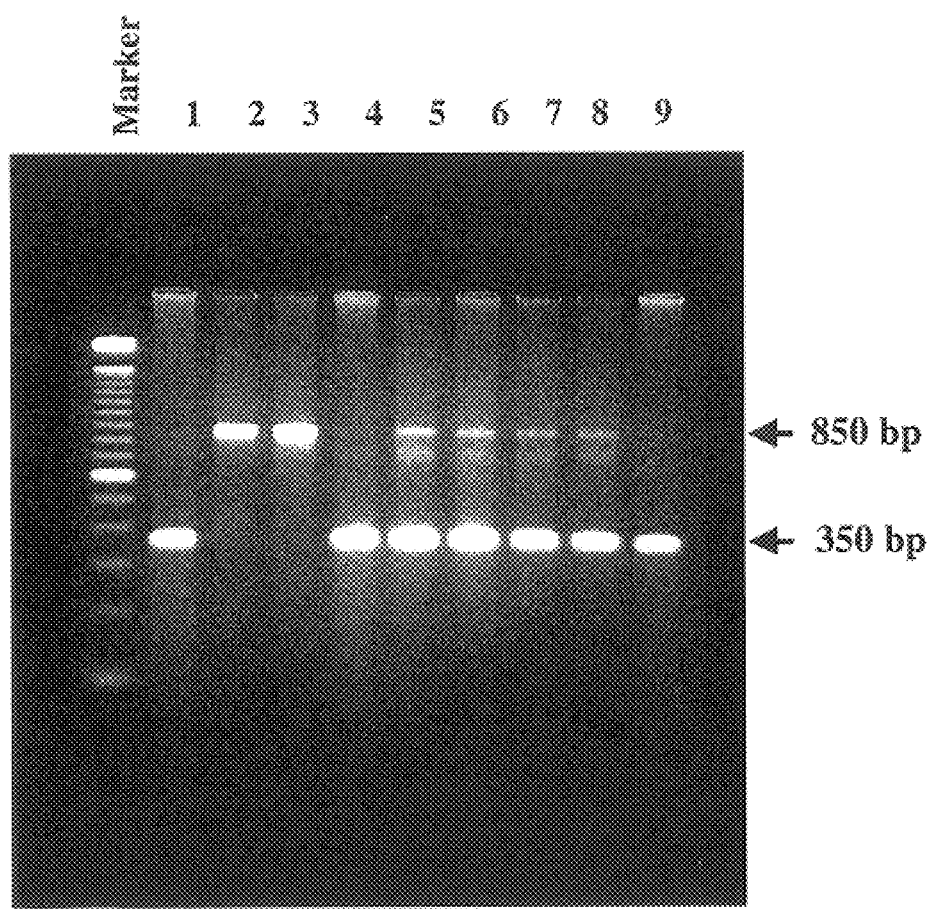
FIG. 2 shows the results from the PCR analysis of the progeny from double heterozygous parents. Samples 1, 4 and 9 are homozygous for the mutated endogenous COL2A1 gene and are also positive for the human COL2A1 gene.

In one embodiment, transgenic mice with the normal or mutated COL2A1 gene are crossed with the heterozygous mutant mice to obtain double heterozygous hybrids. A schematic of the normal human COL2A1 gene construct is depicted in FIG. 1. These double heterozygotes are crossed to obtain mice that are homozygous for the mutation and which also carry either one or both alleles of the human transgene. These animals are identified by PCR analysis as depicted in FIG. 2 using well known techniques routine to those skilled in the art. Such animals are expected at a ratio of 2:16 and 1:16, respectively.

Example 4

Collagen Type II Biomaterial for Somatic Cell Therapy

Chondrocytes are isolated from cartilage tissue from 8 to 10 pups within 2–3 days of birth or xiphoid cartilage from 4–6 adult mice. Epiphyseal cartilage is removed from the femoral heads in accordance with well known procedures, such as those described by Vandenberg et al. (1991) *Proc. Natl. Acad. Sci. USA,* 88:7640–44, under sterile conditions. The chondrocytes are isolated from xiphoid tissue. In this procedure, the adherent fibrous tissue from cartilage is removed by incubating in Hank's medium containing trypsin and bacterial collagenase (2 mg/ml each) for 1 hour at 37° C. The medium is discarded and other tissue fragments are minced and digested overnight at 37° C. The medium is discarded and other tissue fragments are minced and digested overnight at 37° C. in Dulbecco's modified minimum essential medium (DMEM) with 4.5 grams/liter glucose containing 10% fetal bovine serum (FBS) and 0.5 mg/ml bacterial collagenase. The cells released by enzymatic digestion are filtered through nylon membrane into a vessel containing DMEM and 10% FBS. The cells are collected by centrifugation at 250×g for 5 minutes, resuspended and washed 4 times with collagenase free medium. The average yield is generally about $3.0 \times 10^8$ chondrocytes/gram of wet cartilage.

The chondrocytes are plated at a density of $5 \times 10^6$ cells in 60 mm plastic petri dishes coated with 0.9 ml of polyHEMA (PolySciences Inc. Malvern, Pa.). Under these conditions, the chondrocytes maintain chondrocyte-specific phenotype for up to 180 days and form nodular structures that resemble mature articular cartilage morphologically and ultrastructurally and maintain high level of expression of cartilage specific genes such as collagen types II, IX and XI and proteoglycan aggarecan without the expression of de-differentiated chondrocyte product type I collagen.

For the preparation of polyHEMA petri dishes, 0.9 ml of a 10% (v/v) solution of polyHEMA in 95% ethanol is layered onto 60 mm bacterial culture dishes and allowed to dry overnight under a tissue culture hood. The polyHEMA coated dishes are sterilized by exposure to ultraviolet light for 30 minutes. The culture medium contains DMEM with 4.5 grams/liter glucose, 10% FBS, 1000 units/ml penicillin, 1 mg/ml streptomycin, 2 mM glutamine, 1% vitamin supplements, 2.5 µg/ml fungizone and 50 µg/ml ascorbic acid. The medium is changed every 3–4 days.

While the present invention has been described in terms of specific embodiments, it is understood that variations and modifications will occur to those skilled in the art. Accordingly, only such limitations as appear in the appended claims should be placed on the invention.

What is claimed is:

1. A transgenic COL2A1-null mouse whose genome comprises a nucleic acid sequence encoding human COL2A1 operatively linked to a promoter, wherein the mouse has i) cartilage comprising human COL2A1 but not mouse COL2A1, and ii) a normal skeletal structure.

2. A composition comprising chondrocytes comprising human COL2A1 but not mouse COL2A1, wherein said chondrocytes are isolated from the transgenic COL2A1-null mouse of claim 1.

3. A composition comprising chondrocytes prepared by the process of:
   (a) raising a transgenic COL2A1-null mouse whose genome comprises a nucleic acid sequence encoding human COL2A1 operatively linked to a promoter, wherein the mouse has i) cartilage comprising human COL2A1 but not mouse COL2A1, and ii) a normal skeletal structure, and (b) isolating chondrocytes from said mouse.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 21
      (B) TYPE: Nucleic Acid
      (C) STRANDEDNESS: Single
      (D) TOPOLOGY: Linear (iv) ANTI-SENSE: NO (xi) SEQUENCE DESCRIPTION: SEQ ID NO: 1:

TTGGGTGTGA TCTGAAGCAT C                                              21

(2) INFORMATION FOR SEQ ID NO: 2:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 2:

AGCCAGCTAA GTCTGTCTGT A                                              21

(2) INFORMATION FOR SEQ ID NO: 3:

(i) SEQUENCE CHARACTERISTICS:
        (A) LENGTH: 19
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 3:

TCGCGATTGA ACAAGATGG                                                 19

(2) INFORMATION FOR SEQ ID NO: 4:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 4:

GAGCAAGGTG AGATGACAGG                                                20

(2) INFORMATION FOR SEQ ID NO: 5:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 5:

GCTATCAGGA CATAGCGTTG G                                              21

(2) INFORMATION FOR SEQ ID NO: 6:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 6:

GGAGTCAGAG CACTGGTCAT G                                              21

(2) INFORMATION FOR SEQ ID NO: 7:

(i) SEQUENCE CHARACTERISTICS:
        (A) LENGTH: 21

```
            (B) TYPE:  Nucleic Acid
            (C) STRANDEDNESS:  Single
            (D) TOPOLOGY:  Linear (iv) ANTI-SENSE:  NO (xi) SEQUENCE DESCRIPTION:  SEQ ID NO: 7:

CTGTTGCTTA TAGGACTCAG G                                              21
```